United States Patent [19]

McGowan

[11] Patent Number: 5,404,228
[45] Date of Patent: Apr. 4, 1995

[54] MISALIGNMENT DETECTION APPARATUS FOR TRANSMISSIOMETER WITH UNDERFILLED REFLECTOR

[75] Inventor: Gerald F. McGowan, Parker, Colo.

[73] Assignee: Monitor Labs, Inc., Englewood, Colo.

[21] Appl. No.: 86,207

[22] Filed: Jul. 6, 1993

[51] Int. Cl.⁶ .............................................. G01N 21/59
[52] U.S. Cl. .................................. 356/438; 250/573; 356/437; 356/439
[58] Field of Search .............. 356/438, 436, 151, 152, 356/153, 438, 437, 439, 121; 250/573, 576

[56] References Cited

U.S. PATENT DOCUMENTS

5,028,790  7/1991  McGowan et al. ................ 356/438

*Primary Examiner*—Vincent P. McGraw
*Attorney, Agent, or Firm*—Fields, Lewis, Rost & Smith

[57] ABSTRACT

In accordance with this invention, a misalignment detector apparatus is provided for a transmissometer with an underfilled reflector. The transmissometer has a transceiver that projects a collimated beam of light of small diameter across a smokestack to a circular reflector of substantially greater diameter than the collimated beam of light so that the reflector is underfilled. The reflector includes apparatus for sensing the position of the collimated beam of light with respect to the center of the reflector and its position on the reflector when it is not on center which allows operator notification of when the beam is on the reflector and when the beam is off the reflector thereby requiring maintenance/realignment.

14 Claims, 6 Drawing Sheets

Fig_3

Fig_4

Fig_5

Fig_6

Fig_7

Fig_8

Fig_9

MISALIGNMENT DETECTION APPARATUS FOR TRANSMISSIOMETER WITH UNDERFILLED REFLECTOR

TECHNICAL FIELD

This invention relates to a device for sensing misalignment of a transmissometer with an underfilled reflector and more particularly to such a device which provides remote read out of such misalignment.

BACKGROUND ART

A common apparatus for measuring pollutants being emitted from a smokestack is a transmissometer having a transceiver on one side of the smokestack and a reflector on the opposite side of the smokestack for reflecting a light beam projected by the transceiver across the stack. The change in the amount of reflected light is indicative of the opacity created by pollutants in the stack stream. Conventional transmissometers of this type over fill the reflector, i.e., the light beam is much larger in diameter than the diameter of the reflector. As long as the light beam is uniform and overlays the entire reflector, no errors in measurement are incurred. However, when misalignment occurs there is movement of the beam around the reflector so that the resultant returned light similarly moves around on the light detector in the transmissometer. Slight non-uniformities in the sensitivity of the detector surface result in measurement errors like non-uniformities in the measurement beam itself. An additional complication arises from the fact that in the overfilled system, the objective lens typically has to be focused to insure that the plane of maximum light uniformity is in the plane of the reflector. The problem with this conventional technique is that it is very difficult to make the light beam uniform and large enough to substantially over fill the reflector. Furthermore, when the reflector is overfilled, the system becomes more inefficient since only a portion of the outgoing light strikes the reflector and is returned to the transceiver.

United States Environmental Protection Agency (EPA) has established performance specifications for opacity monitors which are used to monitor smoke density and smokestacks at regulated facilities. These specifications are described in 40 C.F.R. 60, Appendix B, Perf. Spec. 1. One of the requirements for opacity monitors is that the alignment detection scheme employed be capable of sensing or indicating when the transmissometer transceiver and reflector become misaligned to such a degree that a 2% error in opacity occurs. On typical smokestack installations or duct installations the support structure for the transceiver and reflector are not completely mechanically stable. As a result, the alignment varies with wind, rain, temperature, shock and vibration which typically is caused by imbalances and associated fans and/or motors, aging and corresponding shifts in foundations, and changes in structural stress caused by changing loads on the associated boiler. Thus, it is not uncommon for misalignment of the transceiver and reflector to occur, and if it is not detected and corrected, it causes a degradation in measurement accuracy. The corresponding measurement error results from the light beam, which has varying degrees of spatial non-uniformity, moving around on the reflector surface and in some cases even moving partially off of the reflector surface.

A current practice used for detecting misalignment in an overfilled system is to provide a bulls eye on a frosted glass window upon which the return beam is focused. In some designs, this alignment target is solenoid activated for positioning the bulls eye in the light path when needed for alignment purposes. During normal measurement, the bulls eye is moved out of the path of the light beam. In other designs the target is activated by light from a beam splitter which always receives a portion of the reflected light intensity. With these arrangements, an operator has to be physically present at the transmissometer installation site, which may be well up on the side of the stack. In addition, the operator must peer into an alignment port where he can observe the returned light on a bulls eye screen. Then he must determine if the alignment condition is satisfactory or so far off center to justify realigning the system. This is a subjective evaluation since the observance of the light on the bulls eye is not highly definitive. Further, if there is a lot of thick smoke in the stack and the stack is physically large, it is difficult to see the returned light spot. As a result, the alignment of such apparatus is only rarely checked and even then the ability to decern proper alignment is marginal. Consequently, many such systems continue to operate long after the alignment begins to compromise the measurement accuracy of the system and the operator is unaware of the degradation which occurs.

DISCLOSURE OF THE INVENTION

In accordance with this invention, a misalignment detector apparatus is provided for a transmissometer with an underfilled reflector. The transmissometer has a transceiver that projects a collimated beam of light of small diameter across a smokestack to a circular reflector of substantially greater diameter than the collimated beam of light so that the reflector is underfilled. The reflector includes apparatus for sensing the position of the collimated beam of light with respect to an optical axis passing through the center of the reflector for determining if there is any misalignment.

More specifically, at least one opening will be provided in the reflector at a known location with respect to the center of the reflector and a photodiode is mounted behind the opening for receiving light from the collimated beam. Indicia producing means is connected to the photodiode for producing a signal indicative of the collimated beam which strikes the photodiode to indicate the position of the collimated beam on the reflector. The indicia producing means may provide a remote read out.

Generally, this opening will be located at the center of the reflector. In addition, an array of openings can be arranged in a circular pattern around the center opening, the circular pattern having a diameter greater than the diameter of the collimated beam. In addition, to a photodiode located behind the center opening, a pattern photodetector may be mounted behind each of the openings in the array and array indicia means can be connected to the pattern diodes for producing a signal indicative of the collimated beam striking at least one of the pattern of photodiodes to indicate misalignment. In addition, the array indicia means can produce a signal indicative of which pattern photodiodes are being struck with light from the collimated beam to indicate the direction of misalignment. Conveniently, the diameter of the circular pattern is slightly less than twice the diameter of the collimated beam. Preferably, the reflector has a diameter at least four times the diameter of the collimated beam.

The collimated beam may be produced by a gas laser light source which produces a narrow beam of light. This narrow beam of light is expanded through a beam expander lens to about five times its initial diameter to form a collimated beam of light which still has a diameter much smaller than the diameter of the reflector. An aperture is positioned in the path of the collimated beam through which the collimated beam is projected to minimize non-parallel rays and resultant light beam spreading. Conveniently, the aperture can be positioned at the focus of the expander lens. Additionally, the light source can be monochromatic and preferably has a wave length between 500 nm and 600 nm. Also, means can be provided to chop the light so as to differentiate the collimated beam light from ambient light in the device.

With the arrangement just described, a transmissometer can be provided which is very reliable and subject to minimal variations due to slight misalignments between the collimated light beam and the underfilled reflector and which also provides sensing means at the reflector for sensing misalignment.

Additional advantages of this invention will become apparent from the description which follows, taken in conjunction with the accompanying drawings.

BEST MODE FOR CARRYING OUT THE INVENTION

Figure 1:
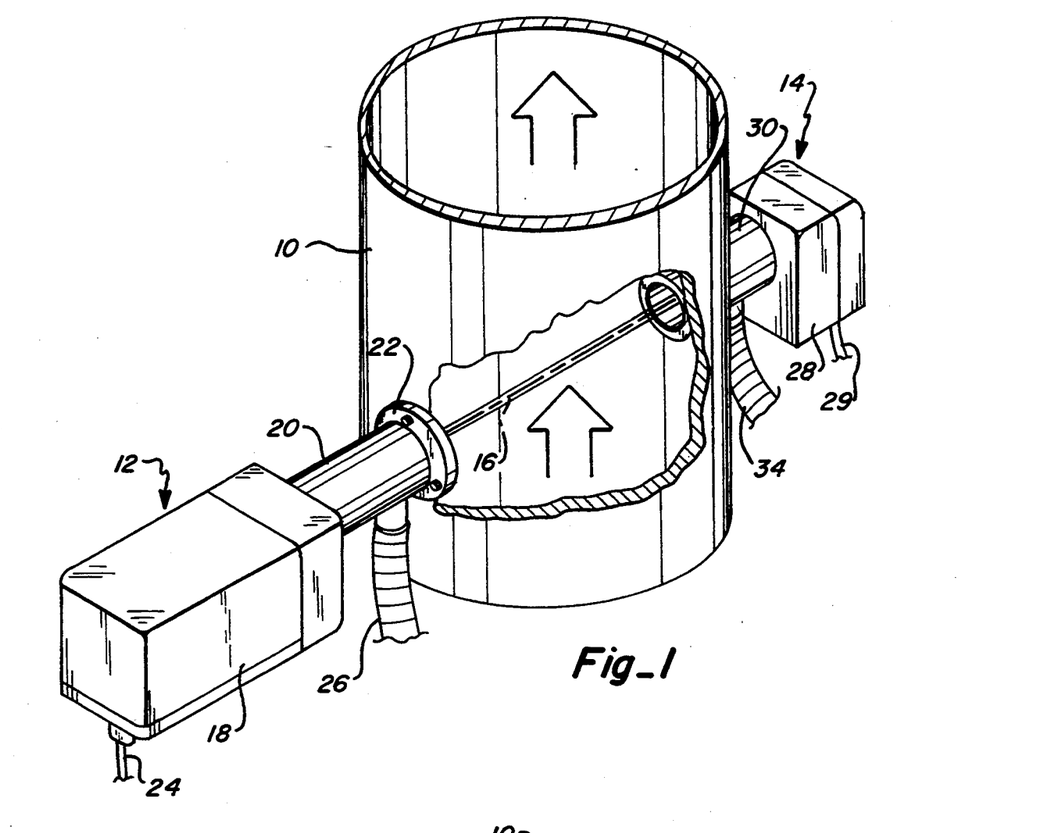
FIG. 1 is a perspective view of a transmissometer constructed in accordance with this invention.
Figure 2:
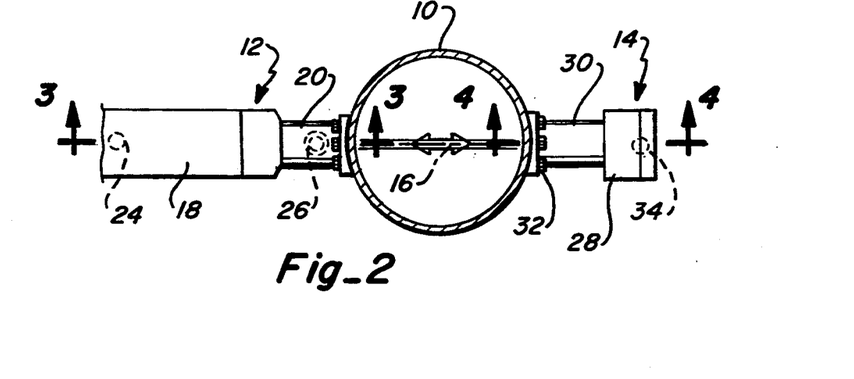
FIG. 2 is a top plan view of the transmissometer of FIG. 1, on a reduced scale.

In accordance with this invention, a transmissometer is attached to stack 10 and has a transceiver 12 mounted on one side thereof and a passive reflector unit mounted on the other side, as shown in FIGS. 1 and 2. As will be more fully explained below, a collimated light beam is transmitted by transceiver 12 across the stack to an underfilled mirror mounted within passive reflector unit 14 along an optical axis 16 which reflects the light back across the stack so that the light will be attenuated in accordance with the amount of the particulate matter in the effluent discharge through the stack. The transceiver 12 includes a weather housing 18 connected to an air purge chamber 20 in the form of a pipe attached to stack 10, as by a flange 22. An electrical connector 24 is provided which extends through weather housing 18 to provide the electrical circuitry for transceiver 12. An air hose 26 is connected to air purge chamber 20 for supplying air under pressure to keep the particulate matter in the stack from entering the transceiver. The air can be exhausted into the stack or through a suitable port (not shown). Similarly, passive reflector unit 14 includes a weather housing 28. An electrical connector 29 is provided which extends through weather housing 28 to provide electrical connections to the alignment sensing photodiodes described below. An air purge chamber 30 connects housing 28 to the stack, as by means of a flange 32. An air pressure hose 34 provides air under pressure to air purge chamber 30 to keep the particulate matter in stack 20 from entering housing 28. The air can be exhausted into the stack or through a port (not shown). Filtered air can be provided by blower 36, shown in FIG. 3, which is drawn through a filter 38 and supplied to the respective hoses 26 and 34.

Figure 3:
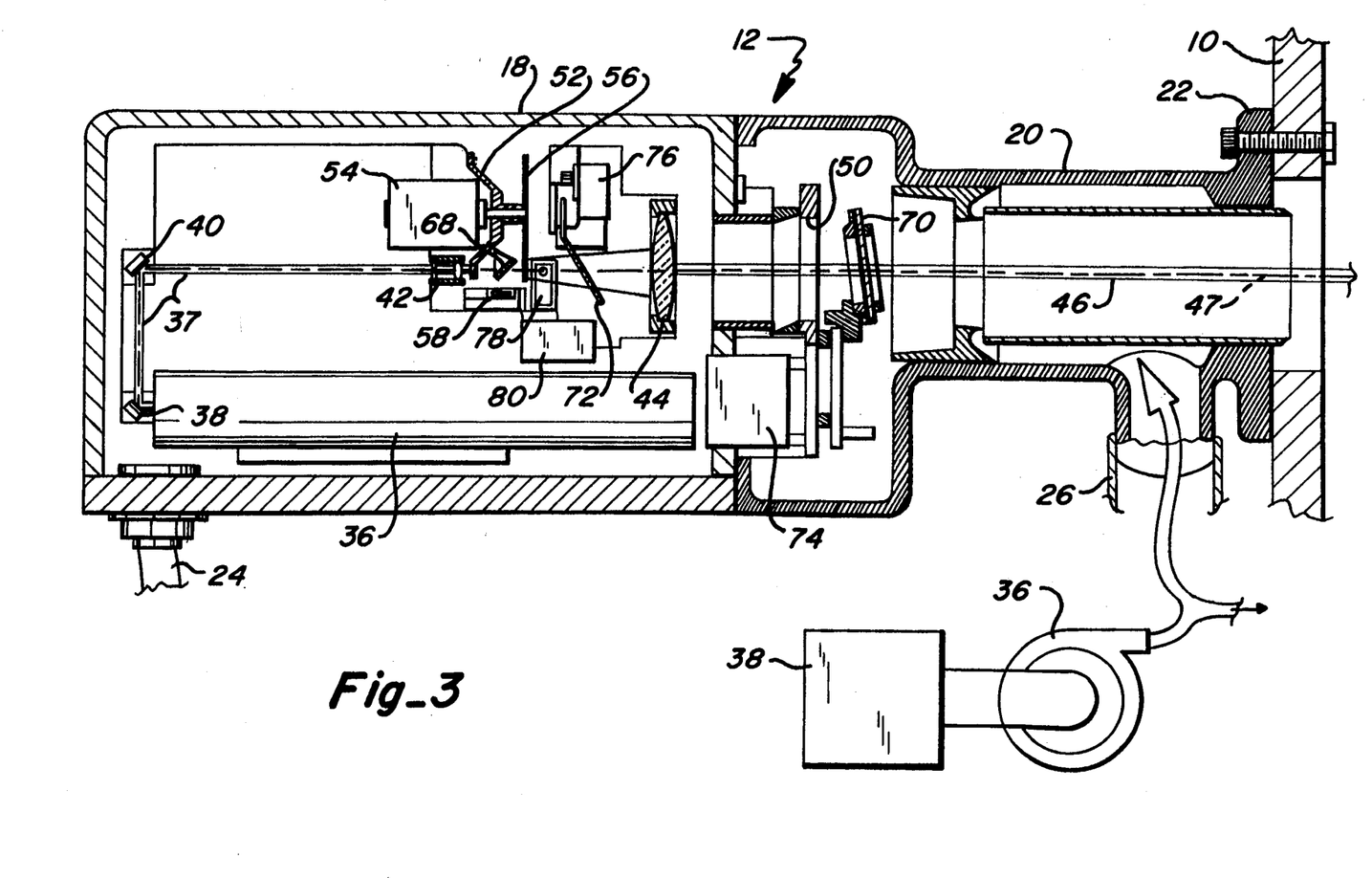
FIG. 3 is a longitudinal section, taken along line 3—3 of FIG. 2, on an enlarged scale, showing details of the transceiver portion of the transmissometer.
Figure 4:
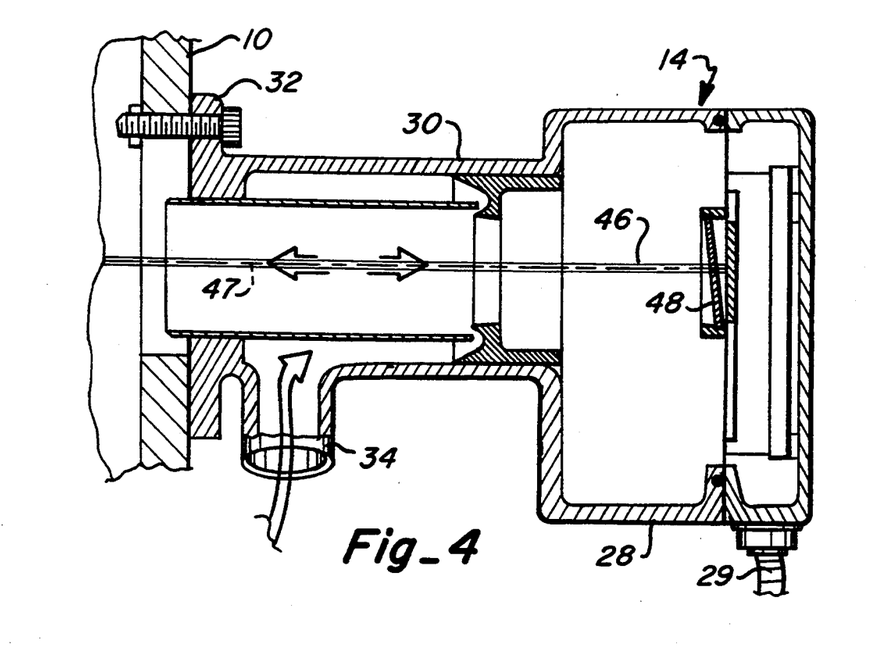
FIG. 4 is a longitudinal section, taken along line 4—4 of FIG. 2, on an enlarged scale, showing details of the underfilled reflector portion of the transmissometer.
Figure 8:
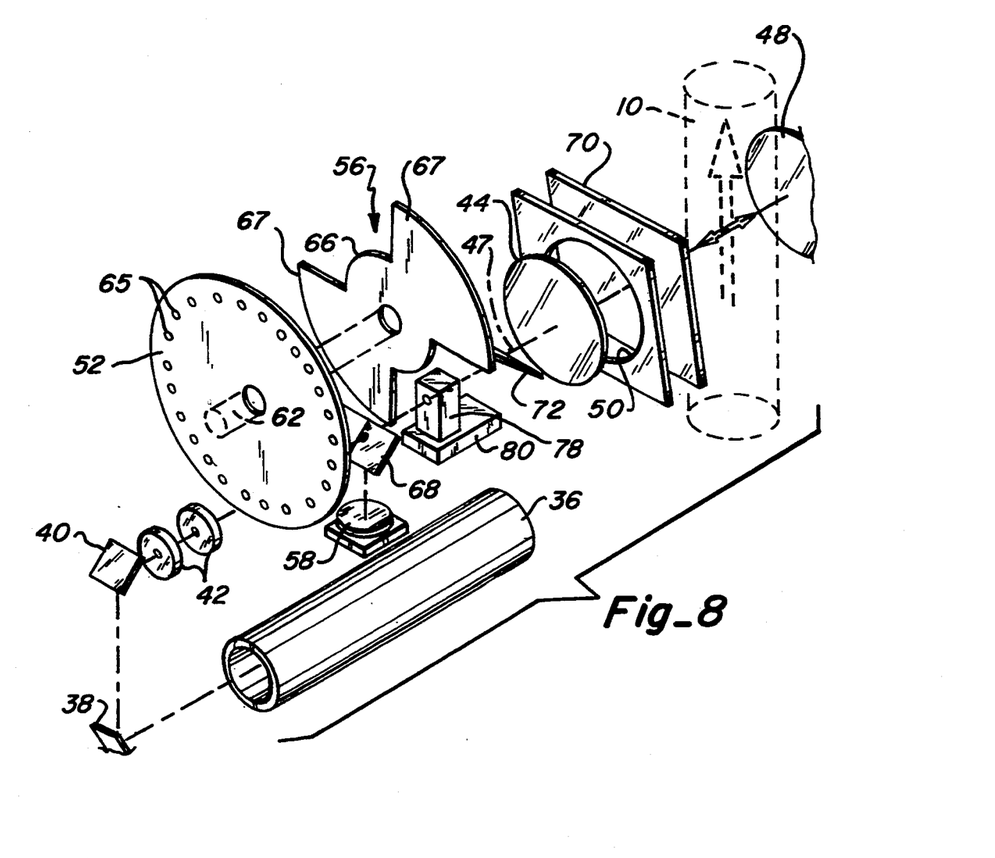
FIG. 8 is a diagrammatic perspective view of the transmissometer of this invention.

As best seen in FIGS. 3 and 8, the light source 36 is a gas filled HeNe laser configured to provide green light at 543.5 nm. Conveniently, light source 36 is located near the bottom of housing 18 and projects a light beam having a diameter of approximately 1 mm which is reflected by mirrors 38 and 40 to reverse the direction of the light beam so that it is projected through expander lenses 42 a diameter of 5 to 5.5 mm. This is accomplished in conjunction with a collimating lens 44 which directs the collimated light beam 46 along longitudinal axis 47 through air purge chamber 20 and stack 10 into reflector unit 14 to be reflected back by an underfilled reflector 48 centered along the same longitudinal axis.

Figure 5:
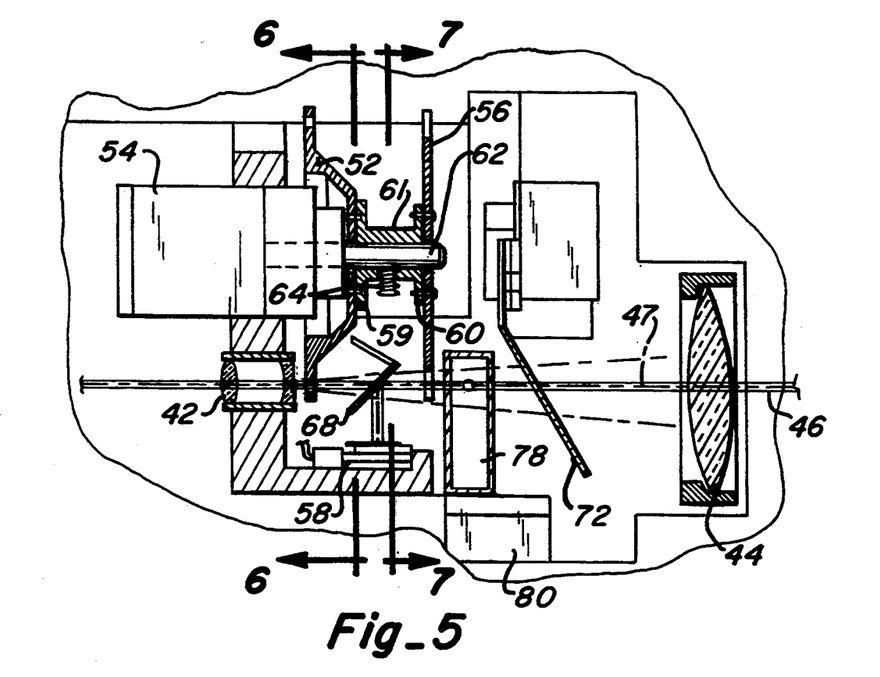
FIG. 5 is a fragmentary enlarged view of the optics portion of the transceiver shown in FIG. 3.
Figure 6:
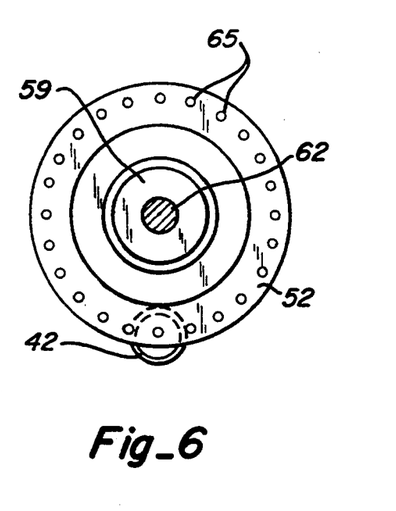
FIG. 6 is a vertical section, taken along line 6—6 of FIG. 5, showing the chopper disk.
Figure 7:
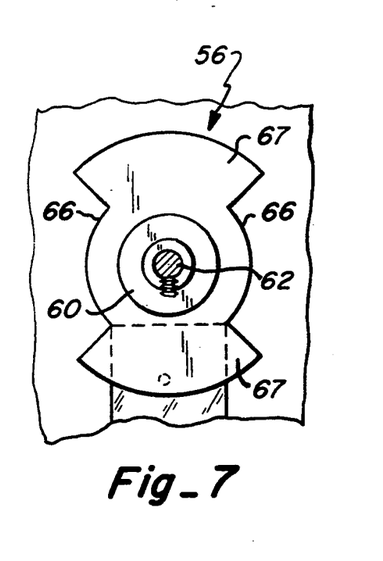
FIG. 7 is a vertical section, taken along line 7—7 of FIG. 5, showing the reference measurement disk.

Conveniently, light beam 46 is projected through an aperture 50 to minimize non-parallel rays and resultant beam spreading. A chopper disk 52 is driven by a chopper motor 54 to modulate the light and allow for separation of ambient light from measurement light. Also, a rotating disk 56 is provided which allows photodetector 58 to be exposed alternately to a measurement beam and the internal reference beam. As best seen in FIGS. 5, 6 and 7, the disks 52 and 56 are attached to end flanges 59 and 60 of a sleeve 61 mounted on chopper motor shaft 62, as by set screw 64. Chopper disk 52 has a plurality of openings 65 around its periphery which allows the light to pass therethrough each time one of the openings is aligned with expander lenses 42. Rotating disk 56 has cut away portions 66 between lobes 67 which alternately interrupt the reflected measurement beam which strikes beam splitter 68 to direct the measurement beam onto photodetector 58. Of course, a portion of projected beam 37, after passing through expander lenses 42 will be diverted by beam splitter 68 onto photodetector 58 also so that comparative readings may be made in a manner that is well-known in the art.

Also included are typical elements of a transmissometer which are required to meet USEPA Performance Specifications for opacity monitors, which are defined in 40 C.F.R. 60 Appendix B, Perf. Spec. 1. These elements include zero calibration reflector 70, a span filter 72. Zero calibration reflector 70 is adjusted to reflect the same amount of light back into the transceiver as the normal reflector does across a clear optical medium of interest as is commonly understood in the art. This adjustment of light level can either be done in the optical domain or in the electrical signals representing the optical intensity, or by using a combination of both. The span filter 72 provides a precise and repeatable level of light attenuation and is used with the zero calibration reflector 70 in place. Both are solenoid or motor activated under either timed, automatic or manual control. Thus, zero calibration reflector 70 is operated by motor 74 and span filter 72 as operated by motor 76, as shown in FIG. 3. Interposed between beam splitter 68 and span filter 72 is an alignment target 78 which is also solenoid activated by solenoid 80. When the solenoid 80 is activated to insert the alignment target into the light path, it shows a relative location of the received light from the reflector 48 with respect to the optical axis 47 of the transmissometer. In this system the alignment target will always show a centered condition since the light is returned along the optical axis.

Conveniently, the laser can be of a single mode output, multi-mode, or random or single plane polarization. Higher order modes are preferred in order to establish a more uniform light intensity across the beam. The beam from such a device is expanded and collimated so that the beam is larger than the irregularities in the reflector medium of reflector 48 and averages out the local irregularities in the selected reflector material. Further, the expanded beam decreases the watt density of the beam thereby reducing the potential for eye damage. With the underfilled reflector approach described above, the reflector is typically many times larger than the measurement light beam. In a typical case, the expander lens 42 has a focal length of 18 mm and the object lens a focal length of 100 mm yielding an expansion of 5.5 or in this case, a beam of 5.5 mm. The beam limiting aperture 50 is ideally positioned at the focus of the beam expander lenses 42 so that the beam remains the same size regardless of the distance across the optical medium of interest, typically a smokestack, such as smokestack 10. The reflector 48 can be either a flat or focused specular mirror or a retroreflective material depending on the application requirements. Typically, the reflector is 50 to 200 mm in diameter. The exact size is selected to provide the desired degree of tolerance to changes in alignment.

Beam splitter 68 can be of conventional construction with a typical 50/50 beam split, a conventional front surface mirror with a centerline hole to allow the outgoing beam to pass unattinuated, a ruled reflecting beam splitter with a centerline hole positioned normal to the beam with the detector relocated to pickup the 45° off-axis reflection or a "polka dot" type of reflector which has small dot type coded reflectors located on a grid wherein the dot diameter to dot spacing is selected to provide the desired 50/50 beam split. The typical 50/50 beam split ratio mentioned above is not critical and can be different to optimize other parameters.

The chopper disk 52 typically consists of a rotating disk which contains 48 holes, each having a diameter of approximately 2 mm. This disk then alternately allows the light to pass through and block the light beam so that ac signal detection means can be used to minimize noise and dc offsets, and so that the resultant measurement of opacity becomes independent of the ambient light level in the vicinity of the measurement. Chopping the light source can also be done by electrically modulating the voltage or current into the laser.

The reference/measurement disk 56 contains two lobes 67 which are covered with a defuse reflective material and reflect the outgoing light back into the detector when interposed in the light beam. These lobes are located in opposite quadrants of the disk, as shown in FIGS. 7 and 8. In the other quadrants, the disk has cut-outs 66 so that the light beam passes unobstructed through the optical medium of interest to the reflector 48 and back into transceiver 12. As this light enters the transceiver, it is focused by the collimating lens 44 and reflected by the beam splitter 68 onto photodetector 58. Alternately, the photodetector sees the internal reference beam and the measurement beam. The above scenario is the preferred configuration since only one detector is used to measure both the reference and the measurement beam. An alternative configuration could use two separate detectors, one for the reference beam and the other for the measurement beam.

The resulting measurement and reference electrical signals are synchronously detected or simply converted to a dc signal by an absolute value circuit and separated into reference and measurement voltages. By taking the ratio of the measurement signal to the reference signal, a ratiometric measurement of the transmittance of the optical medium is obtained. By having previously established the clear path transmittance and setting it to 100%, the change/decrease in transmittance can be converted to opacity. Since the optical medium of interest is traversed twice, the transmittance is converted to optical density. The optical density as measured is divided by two to account for the double pass measurement and the resultant value is converted to opacity. Further capability is typically provided to multiply the optical density by factors other than 0.5 to account for the fact that the EPA requires opacity corrected to stack exit conditions where the path length at that point is not the same as the diameter of the smokestack at the measurement point. The mathematics involved in converting transmittance to optical density and opacity at the stack exit have been extensively documented in other texts.

By using a small collimated beam 46, the reflector 48 can either be similarly small if no movement of the reflector is anticipated, or the reflector can be much larger than the beam if such movement is probable. When movement of the transceiver and reflector with respect to each other is anticipated, the reflector is made sufficiently large and uniform so that regardless of its movement the beam strikes the reflective material and is returned to the transceiver. In such a case, the reflector is said to be underfilled, as opposed to the more conventional overfilled case. In the case of the underfilled reflector, the system is more optically efficient and the errors due to alignment tolerance only result from reflector non-uniformity. It should be noted that the returned light always returns along axis 47 and reflector surface irregularities are therefore irrelevant. Fortunately, it is possible to obtain reflective materials which are very uniform, allowing substantially tolerance to misalignment. By making the reflector much larger than the impinging light beam, the tolerance to misalignment can be made very large, in fact, much larger than is possible with typical overfilled reflector optical systems.

The preferred reflective material is a grid of very small corner cubes molded into glass or plastic with a front surface coated to enhance reflectivity. This material is made by micro-machining, using diamond tooling, a master surface in molding or replicating the surface in plastic or glass. The individual corner cubes need to be very small so that one hundred or more are covered by the light beam at any particular place on the surface of the reflector. Typical facet-to-facet spacing is 0.010 inches. In this way, if one or two of the corner cubes are faulty, the overall efficiency of the surface is not significantly affected. Overall irregularities in the surface must be reduced to about 1% variation as measured by the impinging light beam. By using the corner cube structure, one also achieves insensitivity to rotational misalignment since a corner cube reflects light back upon itself when fully covered by the light beam. Similar characteristics can be obtained at less cost but with greater non-uniformity using "scotch light®" type materials which have a variety of retroreflective beads deposited on a base material. The photodetector may be provided with built-in optical filters (not shown) to limit the spectrum of radiation to which it is exposed. The filter could also be separate but in any case are selected to pass the selected laser wave length at a minimum and/or to limit the radiation to the desired photo-optic spectra response.

Figure 9:
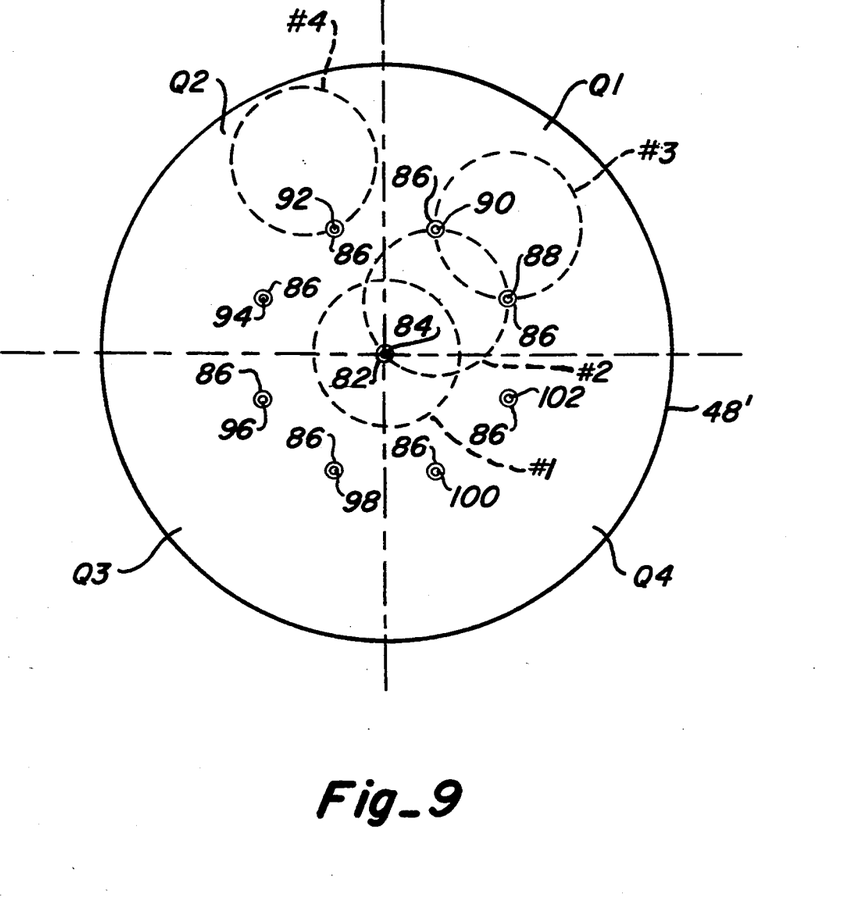
FIG. 9 is a plan view of the underfilled reflector showing apertures therein for photodiodes to detect misalignment.
Figure 10:
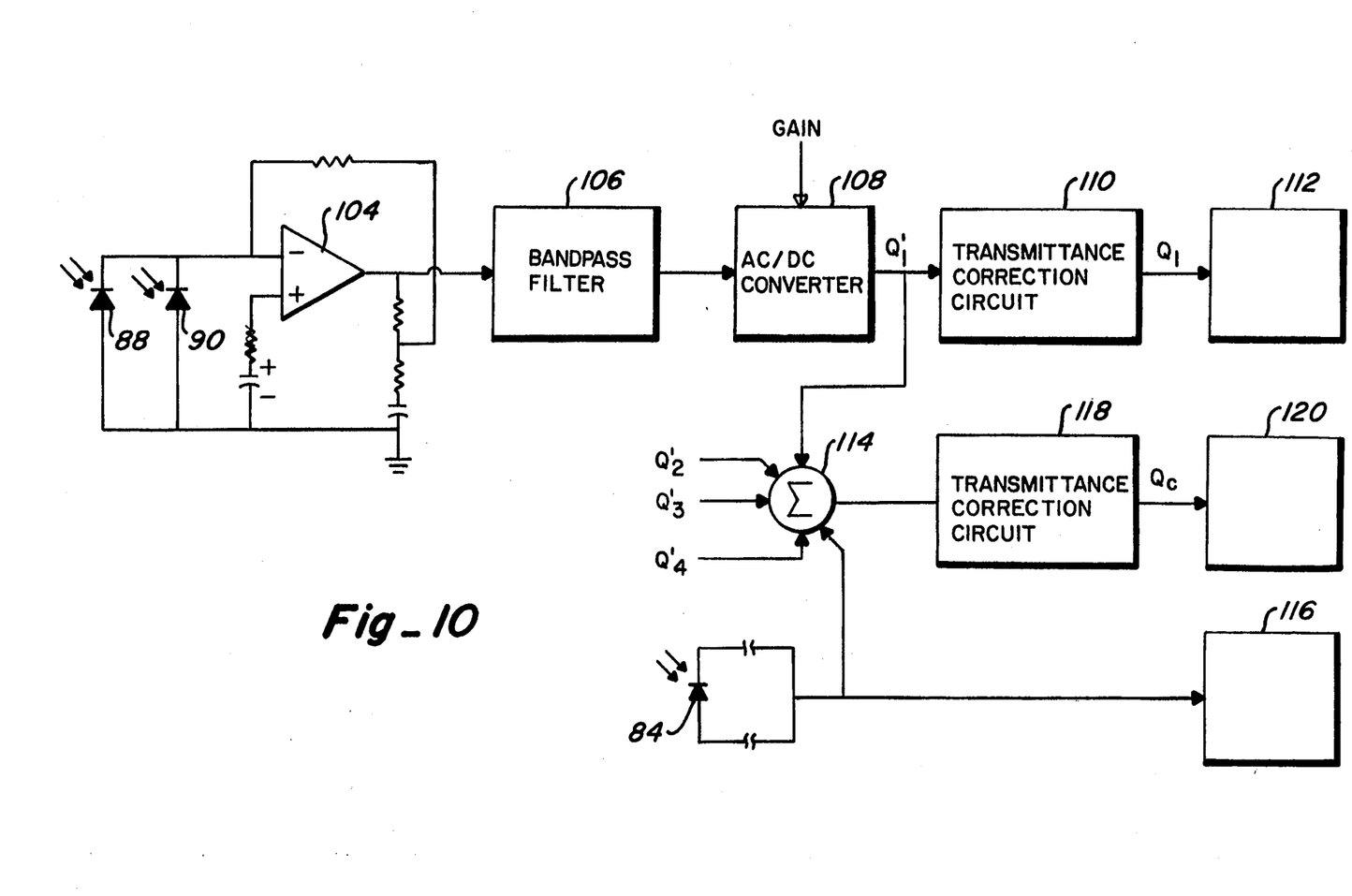
FIG. 10 is a circuit diagram showing the remote read out for the photodetectors.

Another feature of this invention is providing a means for continuous on-line detection of misalignment between transceiver 12 and reflector 48' as described in conjunction with FIGS. 9 and 10. As shown in FIG. 9, reflector 48' has apertures or openings provided in its surface which allow light to pass through it to photodiodes located directly behind the apertures. The apertures must be small enough with respect to the size of the beam that they do not substantially affect the efficiency of the reflector surface. They must be located in a prescribed manner so that the projected light beam impinges on at least one photodiode when the beam is completely contained on the reflector surface or, conversely, so that none of the photodiodes are illuminated when the beam approaches the edge of the reflector surface. Thus, a center opening or aperture 82 is provided to allow light to pass through to photodiode 84, which provides an indication when at least a portion of the projected light beam is striking the center of the reflector surface. Surrounding center opening 82 are a plurality of apertures or openings 86 in a circular array which are located a distance from the center opening 82 which is slightly smaller than twice the diameter of the collimated light beam 46. With this arrangement, the reflector 48 should be about four times the diameter of collimated light beam 46. The exact diameter of the array of openings 86 is a function of the number of diodes in the circular array which may be from four to eight or more. Behind each opening 86 is a diode. As shown in FIG. 9, the reflector 48 can be divided into quadrants Q1, Q2, Q3 and Q4. Thus, behind the openings in quadrant Q1 are diodes 88 and 90. Similarly, behind the openings 86 and quadrant Q2 are diodes 92 and 94, respectively. In quadrant Q3, diodes 96 and 98 are positioned behind openings 86 and in quadrant Q4 diodes 100 and 102 are positioned behind openings 86. Conveniently, this ring of diodes may be connected in parallel for each quadrant.

The circuitry for quadrant Q1 is shown in FIG. 10. In quadrant Q1, photodiodes 88 and 90 are connected and parallel through amplifier 104 which supplies a signal to a band pass filter 106. The signal from band pass filter 106 is supplied to AC/DC converter 108 which provides an output signal $Q'_1$. Signal $Q'_1$ is divided in half by transmittance correction circuit 110 since the light striking the diodes has only passed through the stack in one direction. The output signal from transmittance correction circuit 110 is supplied to a suitable readout device 112. The signal $Q'_1$ is also provided to a summation device 114.

Similar circuits would be provided for quadrants Q2, Q3 and Q4, but have not been specifically illustrated. The output from each of these quadrants would be provided to a readout device like readout device 112 and the signal from the respective AC/DC converters $Q'_2$, $Q'_3$ and $Q'_4$ are each provided to summation device 114. Likewise, center photodiode 84 will be connected to similar circuitry and will provide an output to summation device 114 and to a readout device 116. Summation device 114 provides a signal to a transmission correction circuit 118 which divides the signal $Q_C$ in half and provides a composite signal to a readout device 120. It will be understood that each of readout devices 112, 116 and 120 may be provided in a single console which allows the operator at a remote location to identify the amount of misalignment of the signal with respect to the center of reflector 48'.

The full scale output from AC/DC converter 108 can be adjusted by adjusting the gain. In a typical situation, a full scale output would be 20 miliamps. The beam is considered centered if the signal from photodiode 85 is greater than 50% of full scale. The device is within normal operating alignment if either the $Q_1$, $Q_2$, $Q_3$ or $Q_4$ signal or the composite signal $Q_C$ or the centered signal is greater than 20% of full scale. The exact position of the beam can be determined from observing on the readouts which is the largest signal for $Q_1$, $Q_2$, $Q_3$, or $Q_4$. A fault or misaligned condition exists if none of the signals $Q^1$, $Q^2$, $Q^3$, $Q^4$ or $Q^C$ are greater than 20% of full scale. With the above setting, the trip level described above may require adjustment to different percentages for specific applications. In FIG. 9, Beam #1 represents a beam which is perfectly aligned on center detector 84. Beam #2 shows a beam which is linearly misaligned from center detector 84 into quadrant Q1 wherein the beam still strikes center diode 84 and quadrant Q1 diodes 86 and 90. Beam #3 misalignment shows further linear misalignment into quadrant Q1 wherein only photodiodes 88 and 90 are illuminated. Should the beam become further misaligned, the operator will be informed that correction of the beam misalignments must be undertaken. Similar alignments could happen in other angular directions, such as in the other quadrants or within two adjacent quadrants, for example as shown by Beam #4.

With the above configuration, the operator of the transmissometer based opacity monitoring system can observe the light intensity on the ring of photodiodes 88, 90, 92, 94, 96, 98, 100 and 102 or on the center diode 84 and know whether it is in a centered alignment condition, in an off-center but still well on the reflector condition, or if the beam is beyond the normal reflector operating area. When the later case occurs, immediate maintenance must be undertaken if the opacity monitoring accuracy is to be maintained.

From the foregoing, it can be seen that a transmissometer which utilizes an underfilled reflector provides more uniform measurement capabilities. When the reflector is provided with photodiodes for providing remote indicia for indicating partial or critical misalignment of the light beam, the operator can be immediately informed and take corrective action as required.

This invention has been described in detail with reference to particular embodiments thereof, but it will be understood that various other modifications can be effected within the spirit and scope of this invention.

I claim:

1. A misalignment detector apparatus for a transmissometer with an underfilled reflector, wherein the transmissometer includes a transceiver mounted on one side of a smokestack and a reflector mounted on the opposite side of the smokestack, the transmissometer directing a beam of light from a light source across the smokestack to the reflector, the light beam being reflected back across the smokestack to the transceiver to measure the capacity level of smoke in the smokestack said apparatus comprising:

means in said transceiver for projecting a collimated beam of light having a small diameter across the smokestack;

a circular reflector having a center and having a diameter that is greater than said collimated beam of light so that said reflector is underfilled; and means on said reflector for sensing the position of said collimated beam of light with respect to said center of said reflector.

2. Apparatus, as claimed in claim 1, wherein said sensing means comprises:

at least one opening in said reflector at a known location with respect to said center of said reflector;

a photodiode mounted behind said opening for receiving light from said collimated beam; and indicia producing means connected to said photodiode for producing a signal indicative of said collimated beam striking said photodiode to indicate the position of said collimated beam on said reflector.

3. Apparatus, as claimed in claim 2, wherein said indica producing means includes:

remote readout means.

4. Apparatus, as claimed in claim 1, wherein said sensing means comprises:

a center opening in said center of said reflector;

an array of openings in said reflector arranged in a circular pattern around said center opening, said circular pattern having a diameter greater than the diameter of said collimated beam;

a center photodiode mounted behind said center opening;

center indicia producing means connected to said center photodiode for producing a signal indicative of said collimated beam striking said center diode to indicate when a portion of said collimated beam is striking said center of said reflector;

a pattern photodetector mounted behind each of said openings in said array; and array indicia means connected to said pattern photodiodes for producing a signal indicative of said collimated beam striking at least one of said pattern photodiodes to indicate linear misalignment.

5. Apparatus, as claimed in claim 4, wherein:

said array indicia means produces a signal indicative of which pattern photodiodes are being struck with light from said collimated beam to indicate the angular direction of misalignment.

6. Apparatus, as claimed in claim 4, wherein:

the diameter of said circular pattern is slightly less than twice the diameter of said collimated beam.

7. Apparatus, as claimed in claim 4, wherein:

said reflector has a diameter at least four times the diameter of said collimated beam.

8. Apparatus, as claimed in claim 1, wherein said means for projecting a collimated beam of light comprises:

a gas laser light source for producing a narrow beam of light;

a beam expander aligned with said source for expanding said light beam to a collimated beam of light having a diameter smaller than said diameter of said reflector; and an aperture positioned in the path of said collimated beam through which said collimated beam is projected to minimize non-parallel rays and resultant light beam spreading.

9. Apparatus, as claimed in claim 8, wherein:

said beam expander is an expander lens having a focal length; and said aperture is positioned at the focus of said expander lens.

10. Apparatus as claimed in claim 8, wherein:

said light source is monochromatic.

11. Apparatus, as claimed in claim 10, wherein:

said light source has a wavelength of 543.5 nm.

12. Apparatus, as claimed in claim 8, further including:

means aligned with said collimated beam to chop the light.

13. A method of detecting transmissometer misalignment, wherein the transmissometer has a transceiver on one side of a smokestack to direct a light beam across the smokestack along an optical axis to a circular reflector which is centered on the optical axis and reflects the light beam back across the smokestack to the transceiver which measures the opacity level of smoke in the smokestack, said method comprising:

projecting a collimated beam of light, having a first smaller diameter, across the stack onto the reflector which is of a substantially greater second diameter than the first smaller diameter of the collimated beam;

sensing any linear misalignment of the collimated beam with respect to the center of the reflector; and providing visual indicia indicative of the amount of misalignment.

14. A method, as claimed in claim 13, including the further step of:

sensing the angular direction of any misalignment from the center of the reflector.

* * * * *